(12) United States Patent
Dana et al.

(10) Patent No.: US 10,548,474 B2
(45) Date of Patent: *Feb. 4, 2020

(54) CALCULATING CONJUNCTIVAL REDNESS

(71) Applicant: Massachusetts Eye and Ear Infirmary, Boston, MA (US)

(72) Inventors: Reza Dana, Newton, MA (US); Francisco L. Amparo Pulido, Cambridge, MA (US); Haobing Wang, Newton, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 18 days.

This patent is subject to a terminal disclaimer.

(21) Appl. No.: 15/856,134

(22) Filed: Dec. 28, 2017

(65) Prior Publication Data

US 2018/0184898 A1 Jul. 5, 2018

Related U.S. Application Data

(63) Continuation of application No. 13/773,310, filed on Feb. 21, 2013, now Pat. No. 9,854,970.

(Continued)

(51) Int. Cl.
*A61B 3/14* (2006.01)
*G06T 7/90* (2017.01)
(Continued)

(52) U.S. Cl.
CPC .............. *A61B 3/14* (2013.01); *G06T 7/0012* (2013.01); *G06T 7/90* (2017.01); *H04N 1/628* (2013.01); *G06T 2207/30041* (2013.01)

(58) Field of Classification Search
CPC ........ G06T 2207/30041; G06T 7/0012; G06K 2209/05; A61B 5/445; A61B 5/004; H04N 1/628
See application file for complete search history.

(56) References Cited

U.S. PATENT DOCUMENTS 4,500,972 A 2/1985 Kuhn
4,668,979 A 5/1987 Jung
(Continued)

FOREIGN PATENT DOCUMENTS

JP 2006-512126 4/2006
JP 2012-517325 8/2012
(Continued)

OTHER PUBLICATIONS

Office Action in Australian Application No. 2015252852, dated Oct. 3, 2018, 9 pages.

(Continued)

*Primary Examiner* — Timothy J Neal
*Assistant Examiner* — Jae Woo
(74) *Attorney, Agent, or Firm* — Fish & Richardson P.C.

(57) ABSTRACT

The present application includes methods, systems and computer readable storage devices for determining a color score for at least a portion of a biological tissue. The subject matter of the application is embodied in a method that includes obtaining a digital image of the biological tissue, and receiving a selection of a portion of the image as an evaluation area. The method also includes determining for each of a plurality of pixels within the evaluation area, a plurality of color components that are based on a Cartesian color space, and determining, from the color components, a hue value in a polar coordinate based color space. The method further includes determining a color value based on the hue value for each of the plurality of pixels, and assigning a color score to the evaluation area based on an average of the color values of the plurality of pixels.

20 Claims, 14 Drawing Sheets

Related U.S. Application Data

(60) Provisional application No. 61/601,484, filed on Feb. 21, 2012.

(51) Int. Cl.
*H04N 1/62* (2006.01)
*G06T 7/00* (2017.01)

(56) References Cited

U.S. PATENT DOCUMENTS

| | | | |
|---|---|---|---|
| 5,016,173 | A | 5/1991 | Kenet |
| 5,243,414 | A | 9/1993 | Dalrymple |
| 5,282,030 | A | 1/1994 | Nishimura |
| 5,291,560 | A | 3/1994 | Daugman |
| 6,337,692 | B1 | 1/2002 | Ral |
| 6,404,916 | B1 | 6/2002 | De La Torre-Bueno |
| 6,438,398 | B1 | 8/2002 | Pflugfelder et al. |
| 6,469,747 | B1 | 10/2002 | Ray |
| 6,535,632 | B1 | 3/2003 | Park |
| 6,728,401 | B1 | 4/2004 | Hardeberg |
| 6,734,899 | B1* | 5/2004 | Okamoto ............... H04N 9/69 348/188 |
| 6,828,981 | B2 | 12/2004 | Richardson |
| 7,215,812 | B1 | 5/2007 | Masaki |
| 7,689,016 | B2 | 3/2010 | Stoecker et al. |
| 7,711,403 | B2 | 5/2010 | Jay |
| 8,009,884 | B2* | 8/2011 | Chio ............... A61B 5/441 382/128 |
| 8,150,501 | B2 | 4/2012 | Stamatas |
| 8,244,004 | B2 | 8/2012 | Free |
| 8,358,812 | B2 | 1/2013 | Free |
| 8,416,258 | B2 | 4/2013 | Lin |
| 8,428,351 | B2* | 4/2013 | Kondo ............... G06T 5/007 358/1.9 |
| 8,588,522 | B2 | 11/2013 | Bhatti |
| 8,626,268 | B2 | 1/2014 | Adler |
| 8,660,323 | B2 | 2/2014 | Free |
| 8,736,685 | B1 | 5/2014 | Dorenbosch |
| 2002/0176099 | A1 | 11/2002 | Gil |
| 2004/0032588 | A1 | 2/2004 | Taylor |
| 2004/0223063 | A1 | 11/2004 | DeLuca |
| 2005/0018226 | A1 | 1/2005 | Chiba |
| 2005/0105796 | A1 | 5/2005 | Hong |
| 2005/0126505 | A1* | 6/2005 | Gallager ............... G02B 27/52 119/234 |
| 2006/0012840 | A1 | 1/2006 | Fukuda |
| 2006/0013478 | A1 | 1/2006 | Ito |
| 2006/0188157 | A1* | 8/2006 | Kondo ............... H04N 1/6058 382/167 |
| 2006/0215907 | A1 | 9/2006 | Shefer |
| 2006/0251323 | A1 | 11/2006 | MacKinnon |
| 2006/0268010 | A1 | 11/2006 | Hadli |
| 2008/0007691 | A1 | 1/2008 | Mihashi |
| 2008/0170764 | A1 | 7/2008 | Burns et al. |
| 2008/0218849 | A1 | 9/2008 | Uhl |
| 2008/0226148 | A1 | 9/2008 | Gu et al. |
| 2008/0260218 | A1 | 10/2008 | Smith et al. |
| 2009/0046928 | A1 | 2/2009 | Kwak et al. |
| 2009/0059326 | A1 | 3/2009 | Hong |
| 2010/0158330 | A1 | 6/2010 | Guissin |
| 2010/0158364 | A1 | 6/2010 | Ma |
| 2010/0204584 | A1 | 8/2010 | Ornberg |
| 2011/0164218 | A1 | 7/2011 | Ornberg et al. |
| 2011/0181746 | A1 | 7/2011 | Free |
| 2011/0182503 | A1 | 7/2011 | Free |
| 2011/0182507 | A1 | 7/2011 | Free |
| 2011/0182509 | A1 | 7/2011 | Free |
| 2013/0079620 | A1* | 3/2013 | Kuth ............... G06T 7/0012 600/407 |
| 2013/0208981 | A1 | 8/2013 | Kong |
| 2013/0226008 | A1 | 8/2013 | Dana |
| 2013/0336557 | A1 | 12/2013 | Cruzat et al. |
| 2014/0010423 | A1 | 1/2014 | Soldatitsch |
| 2015/0036923 | A1 | 2/2015 | Jia |

FOREIGN PATENT DOCUMENTS

| | | |
|---|---|---|
| JP | 2013-544589 | 12/2013 |
| RU | 2422081 | 6/2011 |
| WO | WO 2004/058056 | 7/2004 |
| WO | WO 2010/071898 | 6/2010 |
| WO | WO 2012/061835 | 5/2012 |

OTHER PUBLICATIONS

Office Action in Chinese Application No. 201580022263.5, dated Sep. 18, 2018, 9 pages (English translation).

Abramoff et al., "Image Processing with ImageJ," Biophotonics International (11)7:36-42 (2004).

Efron, "Clinical applications of grading scales for contact lens complications," Optician, 213:26-35 (1997).

Efron, "Grading scales," Optician 219:44-45 (2000).

Gonsales et al., "Mir tsifrovoj obrabotki. Tsifrovaya obrabotka izobrazhenij." Moskva, Tekhnosfera, p. 451, 495 (2005) (with the entire relevant chapter from the corresponding English edition).

International Search Report and the Written Opinion of the International Searching Authority issued in PCT/US2013/027132 dated Jun. 20, 2013 (7 pages).

Schulze et al., "Grading bulbar redness using cross-calibrated clinical grading scales," Invest. Ophthalmol Vis. Sci. 52(8):5812-5817 (2011).

Schulze et al., "The Development of Validated Bulbar Redness Grading Scales," Optom Vis Sci. 84:976-983 (2007).

Tan et al., "Objective quantification of fluorescence intensity on the corneal surface using a modified slit-lamp technique," Eye and Contact Lense, 39: 3, 239-246, May 2013.

Rodriguez et al., "Automated detection and enumeration of corneal superficial punctate keratitis," R & D, Ora, Inc., Andover, MA, U.S., May 8, 2013, 3 pages (Abstract).

Office Action in Chinese Application No. 201580022263.5, dated Nov. 23, 2017, 16 pages (with English translation).

Extended European Search Report in Application No. 15786468.7, dated Nov. 28, 2017, 8 pages.

Office Action in Japanese Application No. 2017-510456, dated Oct. 23, 2018, 13 pages (with English translation).

Periketi, "Gaze Estimation Using Sclera and Iris Extraction," Thesis for the degree of Master of Science in Electrical Engineering, University of Kentucky, College of Engineering, 2011, 37 pages.

Office Action in Japanese Application No. 2017-510456, dated Apr. 24, 2018, 10 pages (with English translation).

Office Action in Chinese Application No. 201580022263.5, dated Apr. 12, 2019, 7 pages (with English translation).

* cited by examiner

FIG. 3C
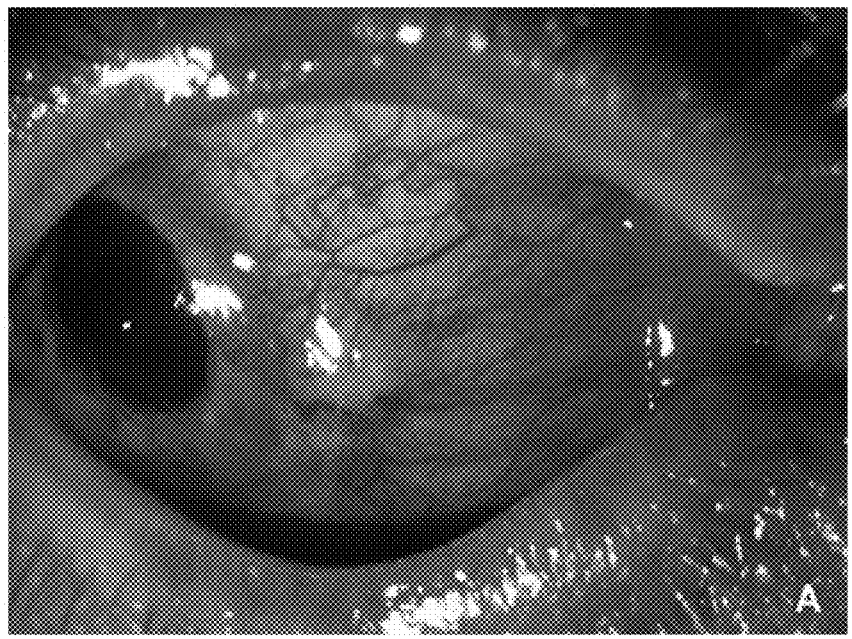
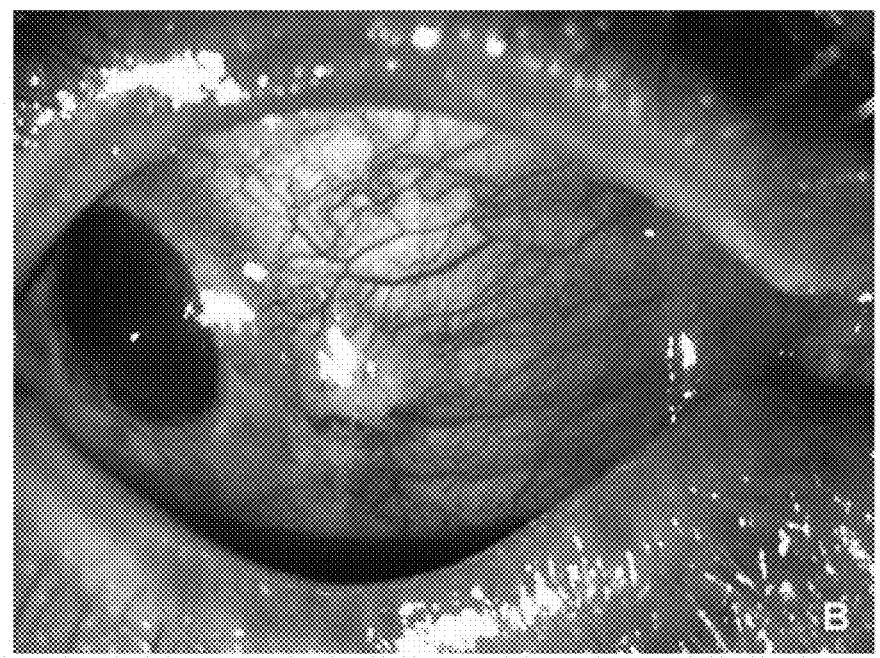
FIG. 3D

CALCULATING CONJUNCTIVAL REDNESS

CROSS REFERENCE TO RELATED APPLICATION

This application is a continuation of U.S. application Ser. No. 13/773,310, filed Feb. 21, 2013, which claims priority to U.S. provisional application No. 61/601,484, filed on Feb. 21, 2012, the entire content of which is incorporated herein by reference.

FEDERALLY SPONSORED RESEARCH OR DEVELOPMENT

This invention was made with Government support under Grant No. K24 EY019098 awarded by the National Institutes of Health. The Government has certain rights in the invention.

TECHNICAL FIELD

This disclosure relates to quantitative determination of a particular color content in an image or a portion of the image.

BACKGROUND

Colored images are often used in medical applications. For example, conjunctival redness has important value in the evaluation of ocular inflammatory or surface disease. Conjunctival redness can be assessed subjectively based on a physician's clinical criteria. Clinicians can guide their criteria using sets of photographs, of which there are different versions and none is considered as a standard. Evaluating conjunctival redness by simple visual observation, whether based on images or direct in-person observation, introduces subjectivity and thus a potential source of bias.

SUMMARY

Described herein are methods and systems that facilitate computer based evaluation of colors in digital images. The digital images can include clinical images or photographs of patients. Selected portions of images taken with different imaging systems can be evaluated with respect to a standardized score that represents specific color content in the selected portions. For example, a portion of a digital image of an eye can be selected to determine a redness score of the selected portion. Such a redness score can be referred to as a Conjunctival Redness Index (CRI) or Ocular Redness Index (ORI). Conjunctival redness can be closely related to ocular redness, and therefore the term CRI may also be interchangeably used with the term Ocular Redness Index (ORI).

In one aspect, this application features a computer implemented method for determining a color score for at least a portion of a biological tissue. The method includes obtaining a digital image of the biological tissue, and receiving a selection of a portion of the image as an evaluation area. The method also includes determining for each of a plurality of pixels within the evaluation area, a plurality of color components that are based on a Cartesian color space, and determining, from the color components, a hue value in a polar coordinate based color space. The method further includes determining a color value based on the hue value for each of the plurality of pixels, and assigning a color score to the evaluation area based on an average of the color values of the plurality of pixels.

In another aspect, the application features a system for determining a color score for at least a portion of a biological tissue. The system includes an imaging system configured to obtain a digital image of the biological tissue, and a color score calculator module. The color score calculator module is configured to receive a selection of a portion of the image as an evaluation area through a user interface. The color score calculator module is also configured to determine, for each of a plurality of pixels within the evaluation area, a plurality of color components that are based on a Cartesian color space, and determine, from the color components, a hue value in a polar coordinate based color space. The color score calculator module is further configured to determine a color value based on the hue value for each of the plurality of pixels and assign a color score to the evaluation area based on an average of the color values of the plurality of pixels.

In another aspect, the application features a computer readable storage device having encoded thereon computer readable instructions, which when executed by a processor, cause a processor to perform several operations. The operations include obtaining a digital image of the biological tissue, and receiving a selection of a portion of the image as an evaluation area. The operations also include determining for each of a plurality of pixels within the evaluation area, a plurality of color components that are based on a Cartesian color space, and determining, from the color components, a hue value in a polar coordinate based color space. The operations further include determining a color value based on the hue value for each of the plurality of pixels, and assigning a color score to the evaluation area based on an average of the color values of the plurality of pixels.

In another aspect, the application features a method of determining severity of an eye condition, wherein increasing severity of the condition is associated with increasing ocular redness. The method includes determining a subject color score for an ocular tissue, wherein the subject color score as compared to a reference color score indicates the severity of the condition. For example, the presence of a subject color score that is above a reference color score indicates that the subject has a severe disease.

In another aspect, the application features a method of monitoring the efficacy of a treatment for an ocular condition in a subject. The method includes determining a first subject color score for an ocular tissue and administering one or more treatments to the ocular tissue. The method also includes determining a second subject color score for the ocular tissue; wherein the first and second subject color scores are determined as described herein. The first and second subject color scores are compared, wherein a decrease in the color scores from the first to the second indicates that the treatment was effective, and no change or an increase in the color scores indicates that the treatment was ineffective.

In another aspect, a method of monitoring the progression of an ocular condition in the subject includes determining a first subject color score for an ocular tissue, and determining a second subject color score for the ocular tissue. The first and second subject color scores are determined as described herein. The method also includes comparing the first and second subject color scores, wherein a decrease in the color scores from the first to the second indicates that the condition is improving, no change in the color scores indicates that the condition is stable, and an increase in the color scores indicates that the condition is worsening.

Implementations can include one or more of the following.

The digital image can include an area of reference white color. A selection of at least a portion of the reference white color can be received and an average gain associated with the portion of the reference white color can be determined. The average gain can be applied to each of the plurality of pixels within the evaluation area. Determining the color value can include mapping an angle corresponding to the hue value to a scalar value within a predetermined range, and determining the color value as a product of the scalar value and at least one component of the polar coordinate based color space that is different from the hue. A parabolic curve can be used in mapping the angle to the scalar value within the predetermined range. The selection of the evaluation area can be received through a graphical user interface in which the digital image is presented. The selection of the evaluation area can be received as a polygonal area of the digital image selected through the graphical user interface. The color score can indicate a degree of redness of the biological tissue. The biological tissue can be an ocular tissue or an epidermal tissue. The ocular tissue can be conjunctiva. The epidermal tissue can be facial epidermis. The Cartesian color space can be an RGB color space. The polar coordinate based color space can be an HSV color space. The color score and an association of the color score with the digital image can be stored in a storage device. The digital images can be related to one or more of corneal neovascularization, fluorescein stained epithelial punctate keratitis and epithelial defects, eyelid and skin telangiectasia, and conjunctival/scleral pigmented lesions.

The user interface can be a graphical user interface in which the digital image is presented. The graphical user interface provides a digital selector for receiving the selection of the evaluation area as a polygonal area in the digital image. The condition can be selected from the group consisting of dry eye syndrome, conjunctivitis, subconjunctival hemorrhage, blepharitis, acute glaucoma, allergy, injury, keratitis, iritis, episcleritis, scleritis, uveitis, inflamed pterygium, inflamed pinguecula, airborne contaminants, Rocky Mountain spotted fever, high stress levels and drug use including cannabis.

Particular implementations may realize none, one or more of the following advantages. Images taken using different imaging systems can be evaluated based on a standardized scale and quantitatively compared with one another. For example, images taken across different imaging systems, lighting conditions, or time can be subjectively compared with one another. This allows for repeatability, consistency and accuracy because the scoring does not rely on the subjective judgment of a human observer, requiring only a personal computer and an operator with basic training on computer use. Evaluation of the images does not require any special training. For example, evaluating conjunctival redness in an eye image using the methods and systems described herein does not require training in ophthalmology. The methods and systems described herein thus provide an objective common denominator that can be used, e.g., to diagnose and to monitor response to therapy, using a computer based analysis. The methods can be used simultaneously in different clinical settings with minimal requirements of technological infrastructure. By allowing for a selection of a custom evaluation area in a digital image, specific areas, e.g., areas including small lesions or the tarsal conjunctiva in an eye image, within the image can be evaluated.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 3C and 3D show two images before and after white balancing, respectively.

DETAILED DESCRIPTION

Evaluating a color content of a digital image has various applications. In some cases, diagnostic or therapeutic procedures can rely on evaluating digital images representing patient conditions. As one example, evaluating conjunctival redness from a digital image of a patient's eye can be important in ophthalmologic applications. Conjunctival redness, also known as bulbar hyperemia, erythema, ocular hyperemia, redness, or injection, is associated with an increased dilation of blood vessels in the conjunctiva, and is a common clinical sign in subjects suffering from a wide range of ocular conditions, such as irritation or an inflammatory response, e.g., due to contact lens wear, medications, or pollutants. In such cases, conjunctival redness can be a useful indicator that can be used, for example, in diagnosis as well as tracking response to treatment.

In some cases, conjunctival redness can be visually evaluated by an ophthalmologist. However, such determination can be inaccurate, subjective and prone to human errors such as bias and inconsistency. Further, images acquired with different imaging systems cannot be reliably compared with one another due to, for example, innate variability across different systems, lighting conditions or time.

Described herein are methods and systems that allow computer based analysis of digital images such that images across different imaging systems, conditions and time can be evaluated based on a standardized score assigned to each of the images. The score assigned to each of the images is based on a particular color content in the image or in a portion thereof. For example, the eye images described above can be evaluated to assign a redness score (referred to herein as a Conjunctival Redness Index (CRI)). The score is calculated such that variability across different imaging systems, conditions and time is accounted for. Therefore, the calculated score serves as a basis for comparing images acquired from various sources. In addition, the methods and systems described herein provide the flexibility of selecting a particular portion of the image to be evaluated.

While this disclosure uses examples of evaluating redness of eye images, the methods and systems described herein can also be used to measure colors in other tissues, e.g., to evaluate corneal neovascularization, fluorescein stained epithelial punctate keratitis and epithelial defects, eyelid and skin telangiectasia (e.g. as in rosacea), and conjunctival/scleral pigmented lesions. Other colors, such as yellowness, can also be measured, e.g., to determine levels of jaundice or other pathological conditions.

Figure 1:
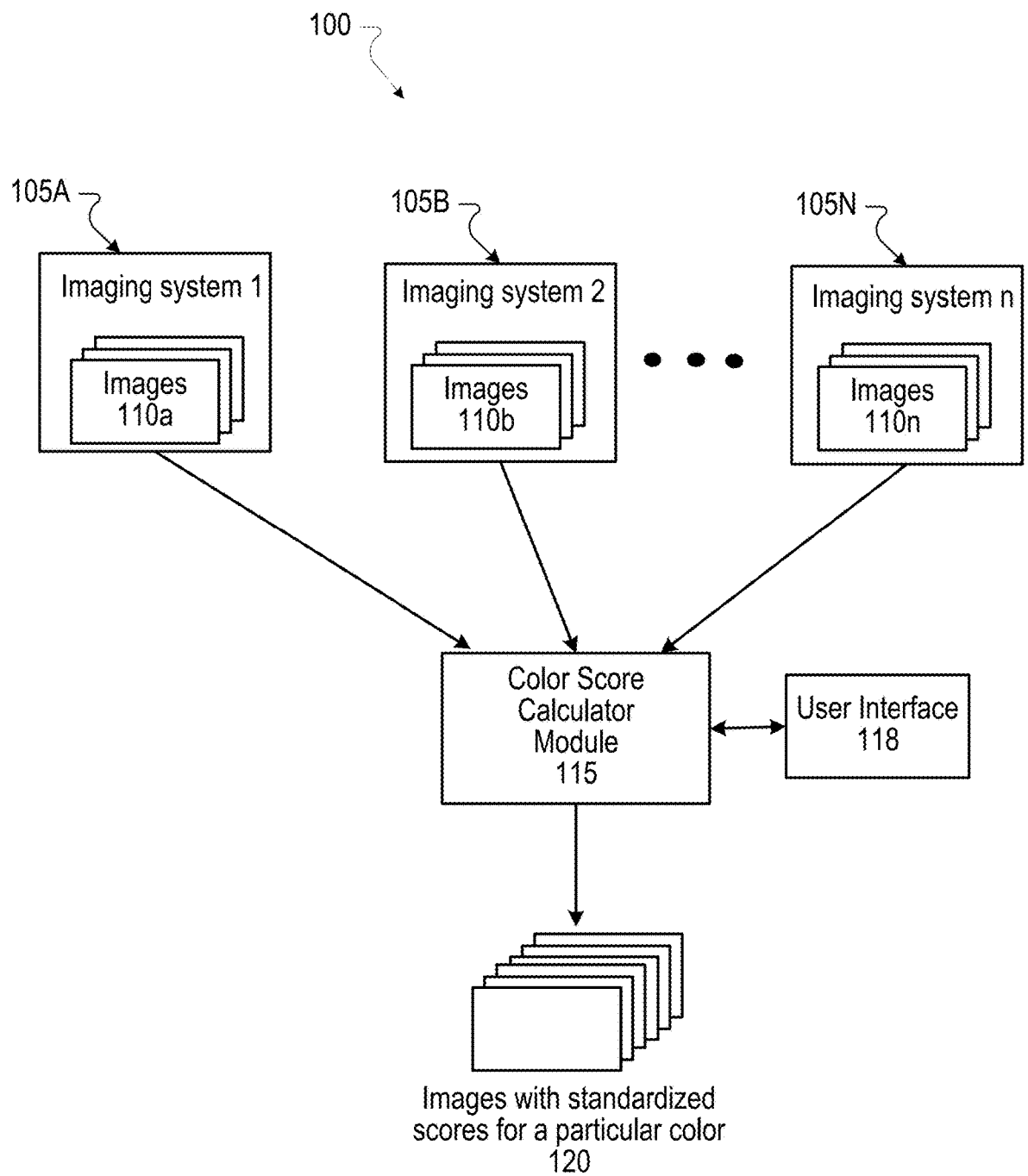
FIG. 1 is a block diagram of an example of a system for calculating color scores of images acquired through different imaging systems.

FIG. 1 shows a block diagram of an example of a system 100 for calculating color scores of images acquired through different imaging systems. The system 100 includes one or more imaging systems 105A, 105B, . . . , 105N (105, in general). The imaging systems 105A, 105B, . . . , 105N are used to acquire images sets 110a, 110b, 110n, respectively (110, in general). The imaging systems 105 can be different or substantially similar to one another. For example, the imaging system 105A can be a slit-lamp camera and the imaging system 105B can be a standard digital photography camera. In another example, the imaging systems 105A, 105B, . . . , 105N can all be slit-lamp cameras of different makes, models or have imaging parameters that are different from one another. The corresponding image sets 110 acquired by the different imaging systems 105 can therefore vary significantly from one another. For example, the images across the different imaging systems 105 can vary from one another in resolution, white balance, lighting characteristics or other image parameters. In such cases, images taken by different imaging systems cannot be reliably compared to one another based simply on visual inspection by a human observer. For example, if two eye images taken by different imaging systems are compared by a human observer, the perceived difference in conjunctival redness may be due to a difference in white balance in the two imaging systems that incorrectly makes one image look redder than the other.

In some implementations, the images 110 acquired by the same imaging system 105 can vary from one another. For example, if the images are taken some time apart, variability due to, for example, parameter drift or different lighting conditions can contribute to the variability of the images.

The system 100 includes a color score calculator module 115 that can be used to determine or assign a color score to the images 110 or to portions thereof. The color score calculator module 115 can be implemented on a computing device and configured to account for variability that exists in images acquired using one or more imaging systems 105. In some implementations, the color score calculator module 115 can be implemented using a general purpose computer such as a desktop or laptop computer or a mobile device that is capable of executing one or more software programs. In some implementations, the color score calculator module 115 is configured to execute one or more image processing application programs such as ImageJ, developed at the National Institutes of Health.

In some implementations, the color score calculator module 115 includes a user interface 118 that is configured to accept user input as well as provide color score outputs to a user. In some implementations, a user can interact with the color score calculator module 115 through the user interface 118. For example, for a given image, the user can select an area of interest over which the color score is calculated. The user interface 118 therefore provides the flexibility of a user choosing a portion of an image (rather than the entire image) over which the color score is calculated. This is advantageous, for example, in eye images where the white scleral/conjunctival region can be selectively chosen over the corneal region in calculating conjunctival redness.

In some implementations, the color score calculator module 115 calculates a color score for the selected region of interest in accordance with one or more image analysis algorithms described below. The image analysis algorithms can include determining color information from pixels of the selected region of interest and/or other portions of the image being analyzed. In general, the color score calculator module 115 assigns color scores to the images 110 or portions thereof and outputs an image set 120 in which each image is associated with a standardized score for a particular color. For example, in case of eye images, the image set 120 can include one or more images 110 that are assigned a corresponding CRI. The images from the set 120 and an association with the respective color scores can be stored in a storage device.

The methods and systems described herein process digital images or portions thereof based on their color properties. Color properties can be described, for example, using color spaces that represent colors as tuples of numbers, typically as three or four values or color components. Examples of color spaces include RGB, CMY, CMYK, YIQ, YUV, YCrCb, HSV, HSI, IHC and HSL color spaces. In general, color spaces can be broadly classified into Cartesian and polar coordinate based color spaces. An understanding of such color spaces is important in the methods and systems described herein and are therefore described next with reference to FIGS. 2A-2D.

Figure 2A:
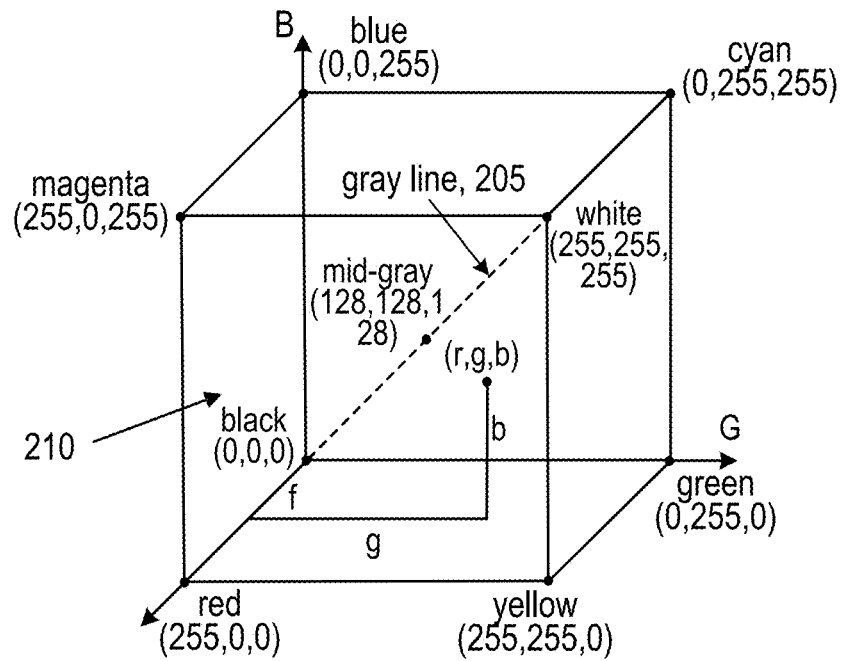
FIG. 2A depicts a Cartesian color space.

Referring now to FIG. 2A, an RGB color space is shown as an example of a Cartesian color space. In this color space, a color is represented in a three dimensional Cartesian space composed on three colors red, green and blue. The RGB color space is an additive color model in which red, green, and blue colors are added together in various ways to reproduce a broad array of colors. The RGB color space is typically used for sensing, representation, and display of images in electronic systems, such as televisions, digital cameras, computers and handheld mobile devices. In the example shown in FIG. 2A, different colors are encoded using three 8-bit unsigned integers (0 through 255) representing the intensities of red, green, and blue. This representation is the current mainstream standard representation in image file formats such as JPEG or TIFF. Such encoding of the RGB space results in more than 16 million different possible colors. As shown in FIG. 2A, the colors at the vertices of the RGB color space may be represented as the following points: (0, 0, 0) is black, (255, 255, 255) is white, (255, 0, 0) is red, (0, 255, 0) is green, (0, 0, 255) is blue, (255, 255, 0) is yellow, (0, 255, 255) is cyan and (255, 0, 255) is magenta. Any point in the volume bounded by these vertices represents a mixed color that can be broken down into red, green and blue components and represented in the RGB space as a point (r, g, b). Further, lines and planes may also be defined in the RGB color space. For example, the line connecting pure black (0, 0, 0) and pure white (255, 255, 255) may be defined as a gray line 205. Other examples of Cartesian color spaces include the YIQ, YUV and YCbCr spaces.

The Cartesian color spaces, while ideal for describing colors in digital formats, are not well suited for describing colors that are practical for human interpretation. For example, human beings do not perceive a color in terms of its component primary colors. Rather, humans usually describe a color by its hue, saturation and brightness or intensity. Hue is an attribute that describes what a color actually is (for example, red, yellow, orange, cyan etc.), whereas saturation is a measure that describes to what extent the color is diluted by white light. Brightness is a descriptor that embodies the achromatic notion of intensity and is an important factor in describing color perception. Color spaces based on these attributes of colors are ideal for algorithms related to human perception of color, such as described herein. The IHC (Intensity, Hue, Chroma) color space described with respect to FIG. 2B is an example of such a color space.

Figure 2B:
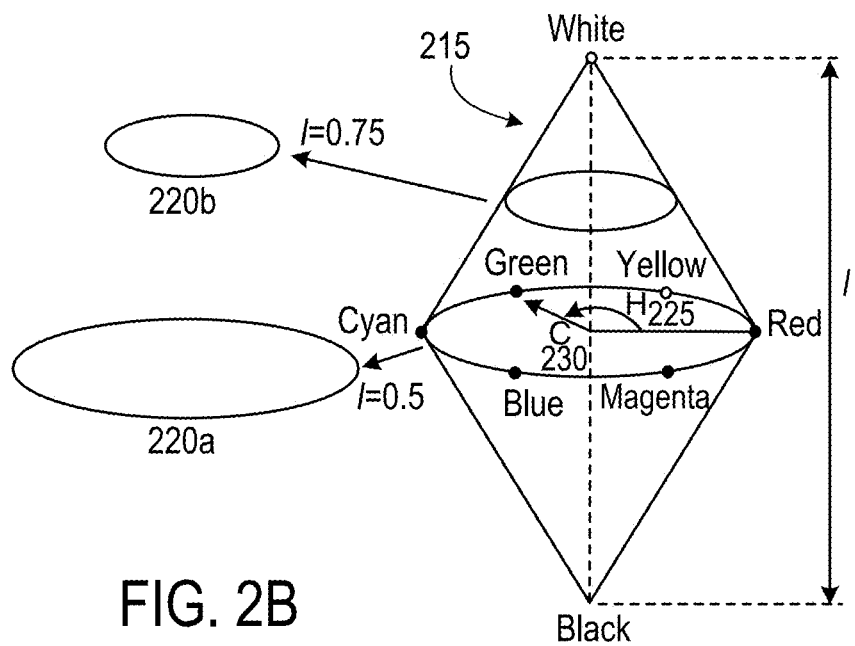
FIGS. 2B-2D depict polar coordinate based color spaces.

Referring to FIG. 2B, the IHC color space includes of a vertical intensity axis 215 and loci 220a, 220b (220 in general) of color points that lie on planes perpendicular to the axis. The hue (H) 225 of a color point within a locus plane (220a for example) is represented by an angle with respect to a reference point while a chroma (C) 230 is represented as a linear distance of the point from the point of intersection of the locus plane 220a with the intensity axis 215. Even though, the example in FIG. 2B shows the loci 220 to be circular in shape, other polygonal shapes, such as triangles, pentagons, hexagons etc., may be used to represent the loci. The area of the loci 220 is a function of the intensity. In other words, the range of chroma is also dependent on the intensity. For example, at zero intensity (i.e. I=0), all colors have zero chroma value and converge to black. Similarly, for the maximum intensity (e.g. I=1), all colors have zero chroma value and converge to white. Within this range, the area of the loci 220 (or the range of chroma values) may increase, for example from I=0 to I=0.5 and then decrease again from I=0.5 to I=1. FIG. 2B shows the locus 220b corresponding to intensity I=0.75. For a given locus plane 220, the hue of a color point is determined by an angle from a reference point. In this example, red designates the reference point, i.e. zero hue, and the hue increases in a counterclockwise direction from the reference point. Other polar coordinate based color spaces, such as the HSL (Hue, Saturation, Lightness) and HSV (Hue, Saturation, Value) color spaces, also follow similar principles with hue being represented as an angle in an polar coordinate based coordinate system.

Figure 2C:
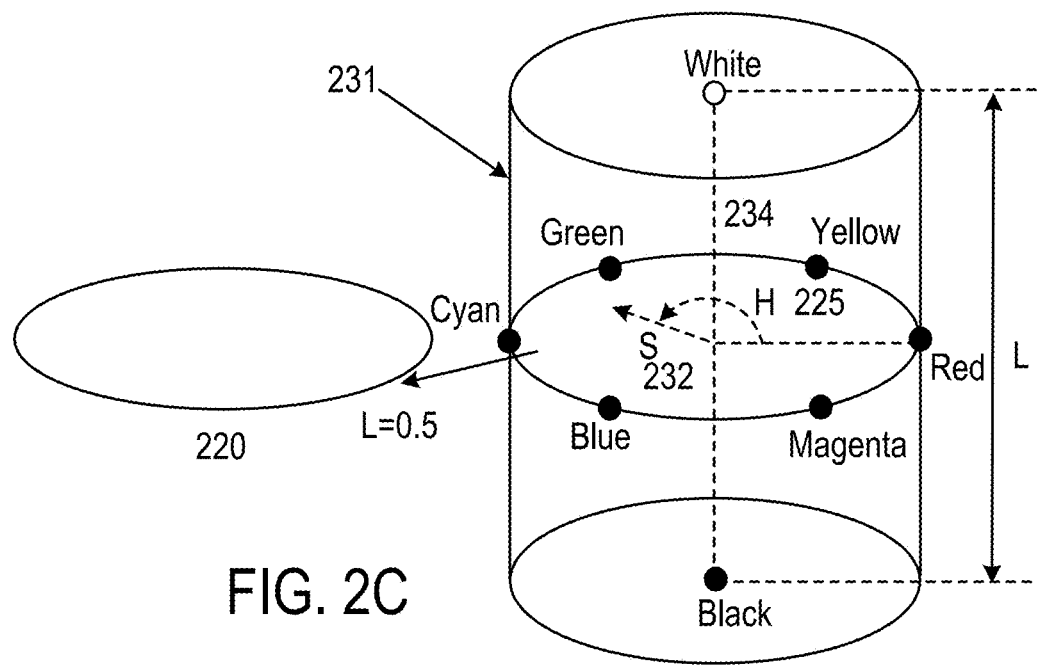

Referring now to FIG. 2C, a HSL color space also includes of a vertical axis and loci 220 of color points that lie on planes perpendicular to the axis. In this color space, the vertical axis represents lightness (L) 234. The HSL color space is also referred to HLS or HSI with I standing for intensity. The HSL color space represents colors as points in a cylinder 231 (called a color solid) whose central axis 234 ranges from black at the bottom to white at the top, with colors distributed between these two extremities. The angle around the axis corresponds to the hue 225, the distance of a point on a given locus 220 from the axis corresponds to the saturation 232, and the distance along the axis 234 corresponds to lightness or intensity. Unlike the chroma 230 in the IHC color space (FIG. 2A), the range of the saturation 232 is not a function of the lightness or intensity.

Figure 2D:
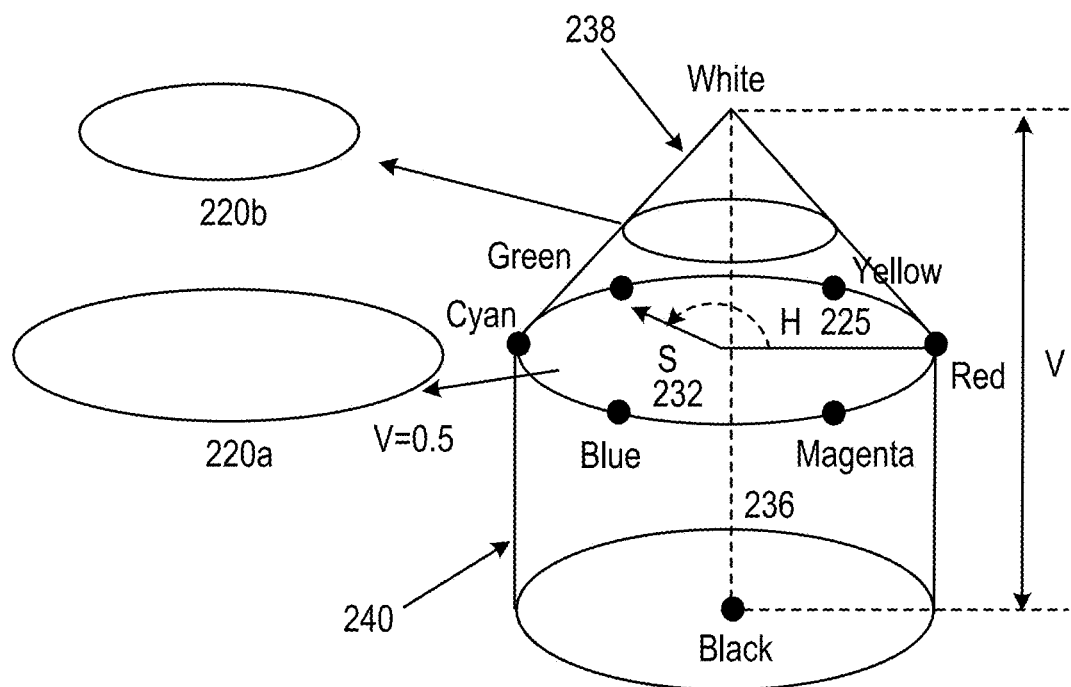

Referring now to FIG. 2D, an example of a HSV color space represents colors via an inverted color cone 238 on a cylinder 240. Other representations of the HSV color space are also possible. In this example, the HSV color space includes a common vertical axis 236 for the cone 238 and the cylinder 240. The central axis 236 ranges from black at the bottom to white at the top, with colors represented in loci 220 distributed between these two extremities. The angle around the axis corresponds to the hue 225, the distance of a point on a given locus 220 from the axis corresponds to the saturation 232, and the distance along the axis 234 corresponds to the value V. The value can be scaled to be between 0 and 1. In this color space, the saturation 232 is a function of the value V when V is between 0.5 and 1. For example, when V=1, all colors converge to pure white. When V is between, 0 and 0.5, the range of the saturation is constant and not a function of the value, as shown in FIG. 2D.

In some implementations, hue information from digital images are used in the methods and systems described herein. In some implementations, color information corresponding to pixels in a digital image are converted to a polar coordinate based color space in determining a color score that represents a particular color content. For example, in determining a redness value for a portion of a digital eye image, the color information from the pixels can be converted from the RGB color space to the HSV color space and the hue information can be used in calculating the redness score of the portion. As described with respect to FIG. 2B, in general, hue is an attribute of polar coordinate based color spaces while most digital images are represented using Cartesian coordinate systems such as the RGB color model. The RGB color information may be transformed into a polar coordinate based color space such as the HSI color space. For example, the hue may be calculated as:

$$H = \begin{cases} \theta & B \le G \\ 360 - \theta, & B > G \end{cases}$$

$$\text{where } \theta = \cos^{-1}\left\{ \frac{\frac{1}{2}[(R-G)+(R-B)]}{[(R-G)^2+(R-B)(G-B)]^{1/2}} \right\}$$

The saturation component is given by:

$$S = 1 - \frac{3}{(R+G+B)}[\min(R, G, B)]$$

The intensity of the component is given by:

$$I = \frac{1}{3}(R+G+B)$$

In some implementations, the RGB color information can be transformed into the HSV color space using the following equations. For example, the value component V can be calculated as:

$$V = \max(R, G, B)$$

The saturation component S can be calculated as:

$$S = \frac{\text{delta}}{\max(R, G, B)} \begin{cases} \text{if} & \max(R, G, B) \neq 0 \\ \text{else} & S = 0 \end{cases}$$

wherein $$\text{delta} = \max(R,G,B) - \min(R,G,B)$$

The hue component H is given by:

$$\begin{cases} \text{delta} \neq 0 & \begin{cases} H = \frac{60 \times \left(\frac{G-B}{\text{delta}}\right) + 360}{360} & \{\text{if } \max(R, G, B) = R\} \\ H = \frac{60 \times \left(\frac{B-R}{\text{delta}}\right) + 360}{360} & \{\text{if } \max(R, G, B) = G\} \\ H = \frac{60 \times \left(\frac{R-G}{\text{delta}}\right) + 360}{360} & \{\text{otherwise}\} \end{cases} \\ \text{delta} = 0 & \{H = 0\} \end{cases}$$

Referring now to FIG. 3, a flowchart 300 represents an example sequence of operations for determining a color score of a digital image. In some implementations one or more of the operations can be executed at the color score calculator module 115 described with reference to FIG. 1.

The operations include obtaining a digital image of biological tissue (302). The digital image can be obtained from an imaging system substantially similar to the imaging system 105 described with reference to FIG. 1. In some implementations, the digital image can be obtained substantially directly from the imaging system. In some implementations, obtaining the digital image can include retrieving the digital image from a storage device. The digital image can include, for example, an image of a human eye wherein the biological tissue is an ocular tissue (for example, conjunctiva). The biological tissue can also be an epidermal tissue (for example, facial epidermis).

Operations can also include receiving a selection of an evaluation area in the image (304). The selection can be received, for example, through a user interface substantially similar to the user interface 118 described with reference to FIG. 1. The selection of the evaluation area (or region of interest) allows a user, in a semi-automated process, to identify a subset of pixels from the digital image for which the color score is calculated. This allows for excluding pixels that are not considered relevant or should be excluded in calculating the color score. For example, in case of determining conjunctival redness from an eye image, the corneal region may be considered irrelevant. In such cases, a user can select the white scleral/conjunctival region from the eye image to be considered in the color score calculation. The selection of the evaluation area also allows a user to modify a shape and/or size of the evaluation as needed. For example, if an eye image shows a red spot in a small portion of the scleral/conjunctival region, calculating the color score based on a small area that just includes the spot can yield a misleadingly high score. However, by including the entire conjunctival area in the color score calculation, a more meaningful score can be obtained. In some implementations, a very specific area can be precisely selected in the image for evaluation, thereby obtaining a score more representative of the selected area than to the complete image. This interactive semi-automatic process also allows for repeatability to evaluate a substantially same area in different images.

The selection of the evaluation area can be implemented using a digital selector functionality of the user interface. In some implementations, the selector function can allow for selecting the evaluation area as predetermined shapes (e.g. circles or rectangles) of adjustable size. In some implementations, the digital selector can allow for selecting more complex shapes such as an irregular polygon. In some implementations, a multi-point selector can allow for selecting any random shapes within the digital image. For example, for measuring a color score related to eyelid and skin telangiectasia images, the evaluation area can be selected as oval. In another example, for measuring a color score in images related to fluorescein stained punctuate keratitis, the evaluation area can be circular. In yet another example, in calculating a color score for images representing corneal or iris neovascularization, the evaluation area can be circular (e.g. to select only the cornea or the iris) or annular. An annular evaluation area can be selected, for example, to exclude the pupil. In such cases, pupil constricting agents can be administered prior to acquisition of the images to minimize variability in pupil diameter. In some implementations, the color score calculation can be based only on pixels within the selected evaluation area.

For each of a plurality of pixels within the evaluation area, the Cartesian color components are determined (306). For example, if the digital image is represented using the RGB color space, the red, green and blue components corresponding to the pixel value are determined. In some implementations, the color components can be associated with another Cartesian color space such as the CMY color space. In some implementations, the plurality of pixels includes all pixels in the evaluation area. In some implementations, only a subset of the pixels within the evaluation is considered in calculating the color score.

Operations further include determining a hue value from the Cartesian color components (308). As described above with reference to FIGS. 2B-2D, hue is a component of a polar coordinate based color space and therefore determining the hue value can include converting the Cartesian color components to a polar coordinate based color space. The polar coordinate based color space can include, for example, the HSV color space. Converting the Cartesian color components to a polar co-ordinate based color space can be done, for example, using the conversions described above with reference to FIGS. 2A-2D. The hue value can be described in terms of an angle also as described with reference to FIGS. 2B-2D.

Figure 3A:
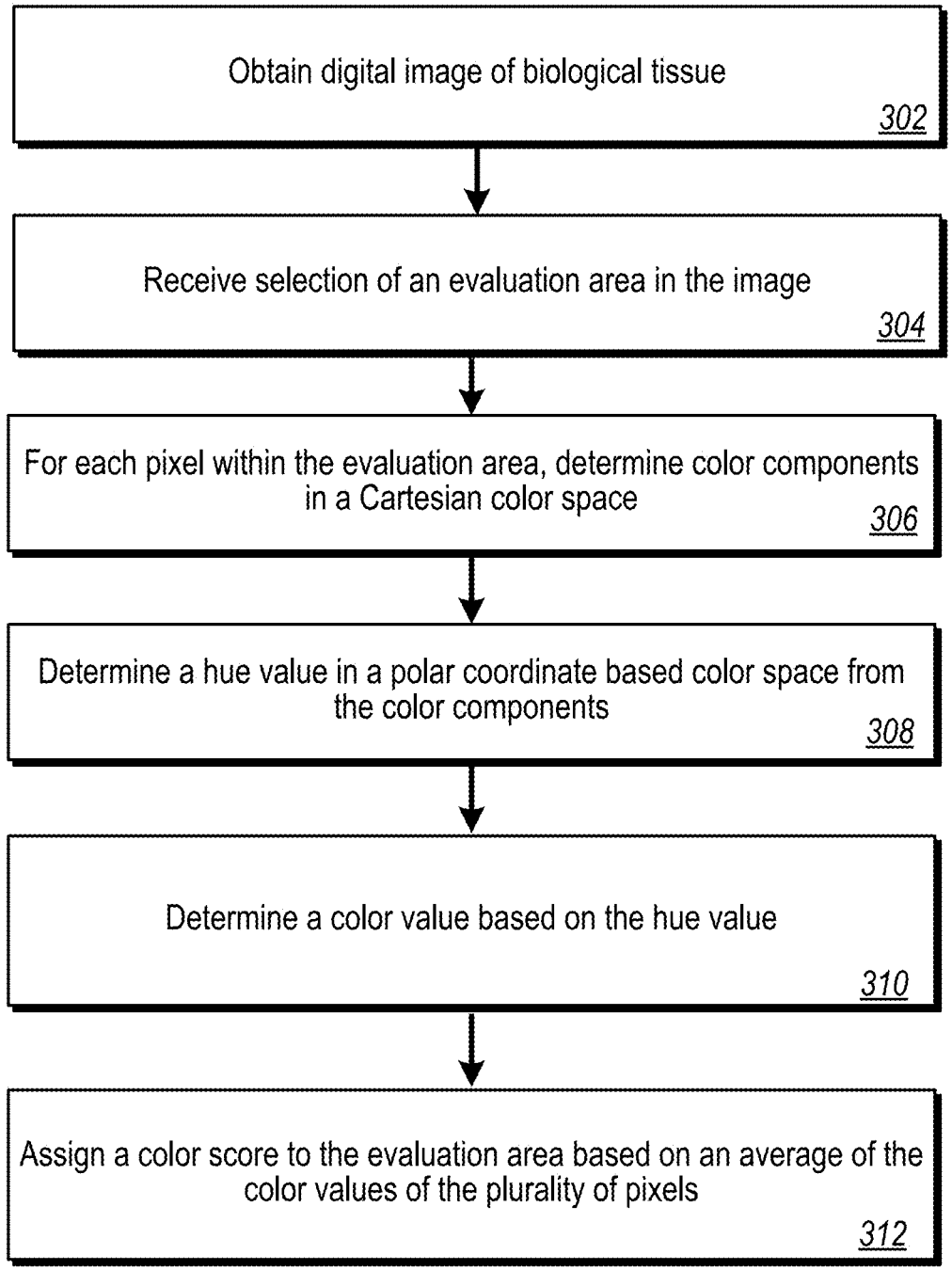
FIG. 3A is a flowchart representing an example sequence of operations for determining a color score of a digital image.
Figure 3B:
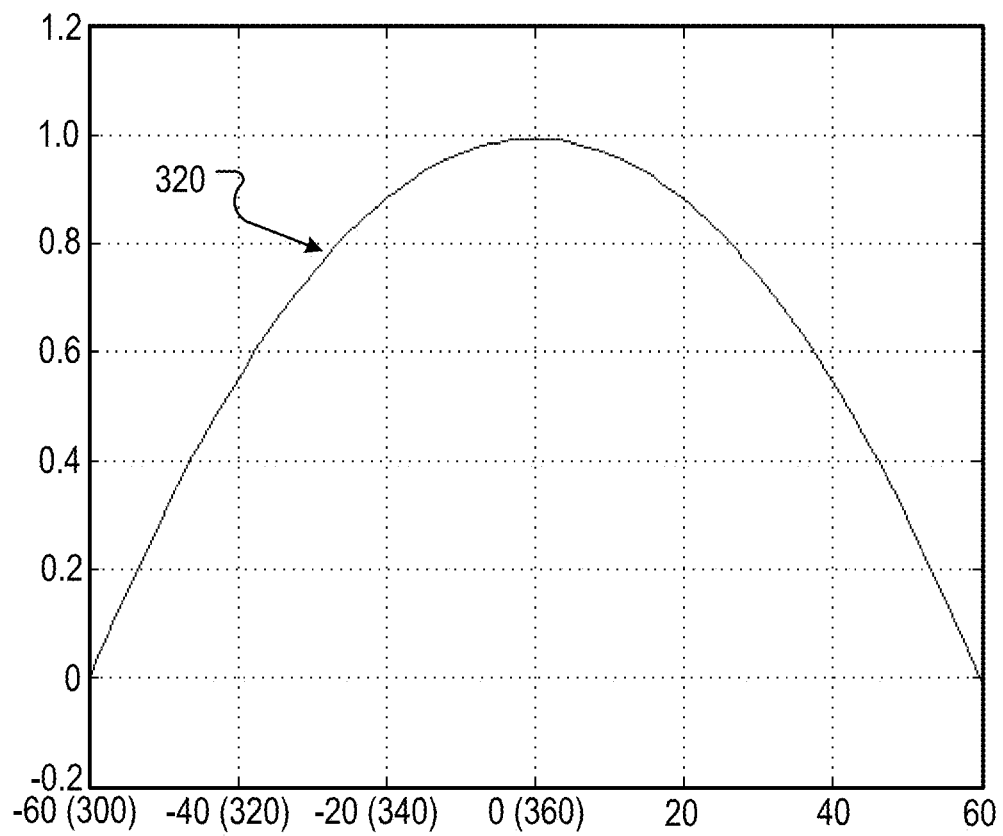
FIG. 3B is an example of a curve used in an operation depicted in FIG. 3A.

Operations also include determining a color value for each of the plurality of pixels (310). In some implementations, determining the color value includes mapping an angle corresponding to the hue value to a scalar value within a predetermined range. For example, in determining conjunctival redness, the hue values corresponding to the color red may lie within −60° and 60°. In some implementations, the angle values can be mapped to a scalar range between, for example, 0 and 1. The mapping may be linear or non-linear. FIG. 3B shows an example of using a non-linear curve such as a parabola 320 to map hue values between −60° and 60° (represented along the x-axis) to a scalar range between 0 and 1 (represented along the y-axis). Other angle ranges can also be used. In some implementations, the angle range that is mapped on to the scalar value can be selected based on a location of a color in the hue circle. For example, in measuring a color score for images related to fluorescein stained punctuate keratitis, an angle range corresponding to observed shades of green (or green-yellow) can be selected. In another example, for images related to conjunctival/scleral pigmented lesions, an angle range corresponding to yellow can be selected. Even for the same color, the selected angle range can vary from one type of image to another. For example, the angle range that is selected for scoring conjunctival redness can be different from the range selected to score redness in eyelid and skin telangiectasia images.

In some implementations, the scalar value itself can be taken as the color value. In some implementations, the color value for a given pixel is determined as a product of the scalar value and one or more components of the polar coordinate based color space. In some implementations, when the HSV color space is used, the color value can be determined as a product of the scalar value with one or both of the S and V components. For example, in scoring conjunctival redness, the color value can be determined as a product of the scalar value and the S component only, whereas in scoring conjunctival/scleral pigmented lesions or fluorescein stained punctuate keratitis images, the scalar value can be multiplied with both the S and V components.

Operations further include assigning a color score to the evaluation area (312). In some implementations, the color score is determined as an average of the color values corresponding to the plurality of pixels for which the color values are computed. In some implementations, other measures of central tendency such as weighted average, median value or mode can also be used in determining the color score. In some implementations, the color score is scaled to a value within a predetermined range (e.g. [0, 100]) before being assigned to an evaluation area. The predetermined range can be chosen based on, for example, the type of image or application. For example, the predetermined range for conjunctival redness can be different from the range associated with corneal neovascularization. In some implementations, the scaling can be such that the highest determined color value maps on to the upper end of the predetermined range (100, in this example) and the lowest determined color value maps on to the lower end of the predetermined range (0, in this example). The color score is then mapped on to an appropriate value within the predetermined range. In some implementations, the predetermined range can be fixed based on predetermined high and low color values. In such cases, color values higher than the highest predetermined value are mapped on to the upper end of the range and color values lower than the lowest predetermined value are mapped on to the lower end of the range. In some implementations, the determined color score is saved in a storage device along with an association that links the score with the corresponding image.

Figure 3F:
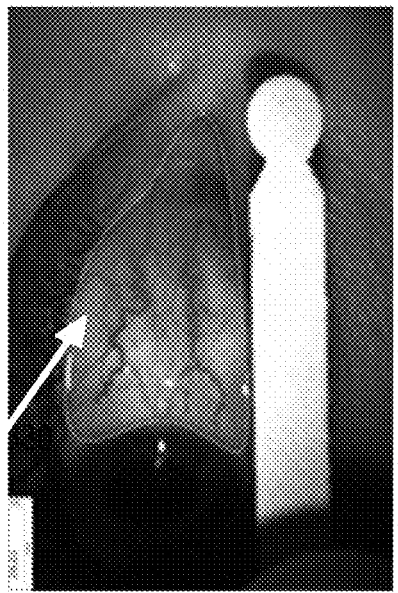
FIGS. 3E-3L illustrate examples of white balancing using a marker.
Figure 3H:
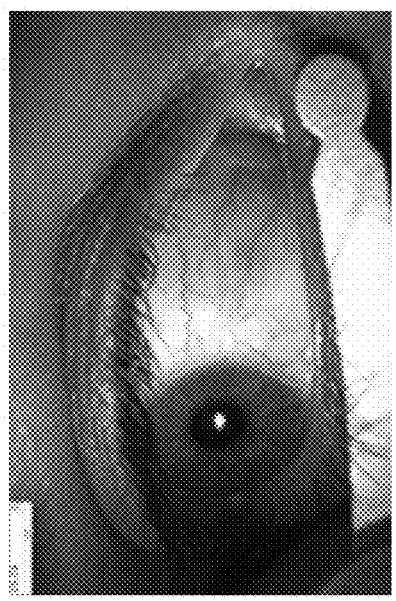
Figure 3E:
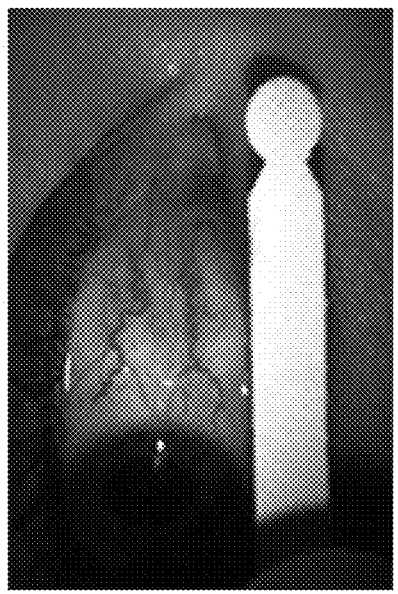
Figure 3G:
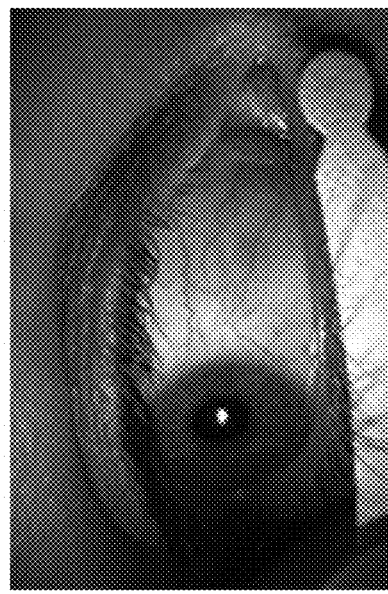
Figure 3I:
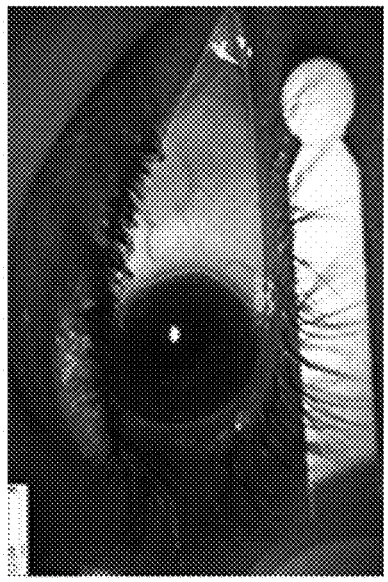
Figure 3J:
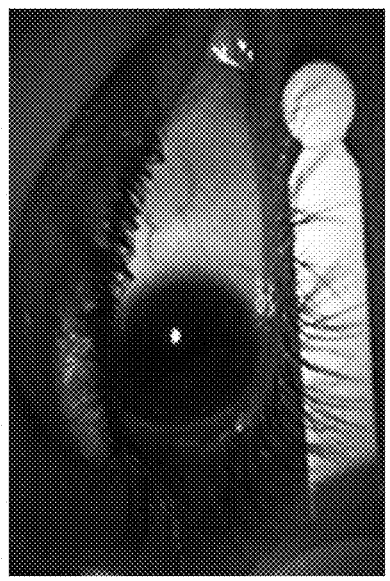
Figure 3K:
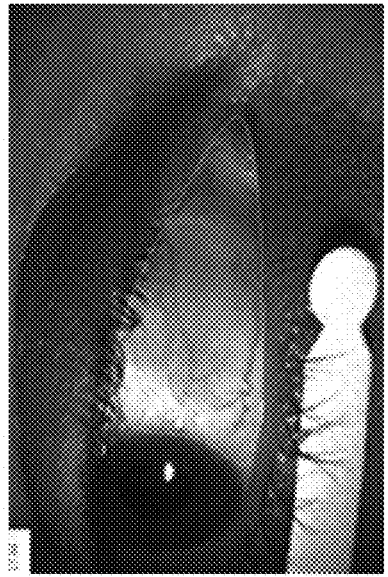
Figure 3L:
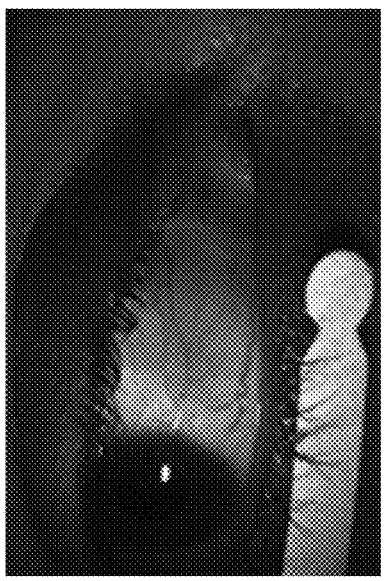

In some implementations, the obtained digital image may be subjected to one or more pre-processing operations prior to calculating the color score. The pre-processing operations can include, for example, noise removal or white balancing. In some implementations, the obtained digital image includes an area of a reference white that is used for the white balance operation. The area of the reference white can be selected from an area of biological tissue represented in the image. This is illustrated in the example shown in FIGS. 3C and 3D. FIG. 3C shows an acquired image before white balancing, and FIG. 3D shows a corresponding white-balanced image. In this example, a spot in the image 3C is chosen as the reference white and the white balancing is performed based on the reference. In some implementations, the area of reference white is selected from a representation of an external marker (e.g., a white background, or a white strip placed in the imaged region) within the image. FIGS. 3E-3F illustrate examples of such use of an external marker. FIG. 3E shows an image that is captured in the presence of an external marker 330. FIG. 3F shows the corresponding white-balanced image wherein the white balancing is performed using a portion of the marker 330 as the reference white. FIGS. 3G-3L show other examples of similar external marker based white balancing, where FIGS. 3G, 3I, and 3K represent the original images, and FIGS. 3H, 3J, and 3L represent the corresponding white balanced versions, respectively. White balancing allows for a gain adjustment across images acquired using different imaging systems and/or at different times or lighting conditions.

Figure 4:
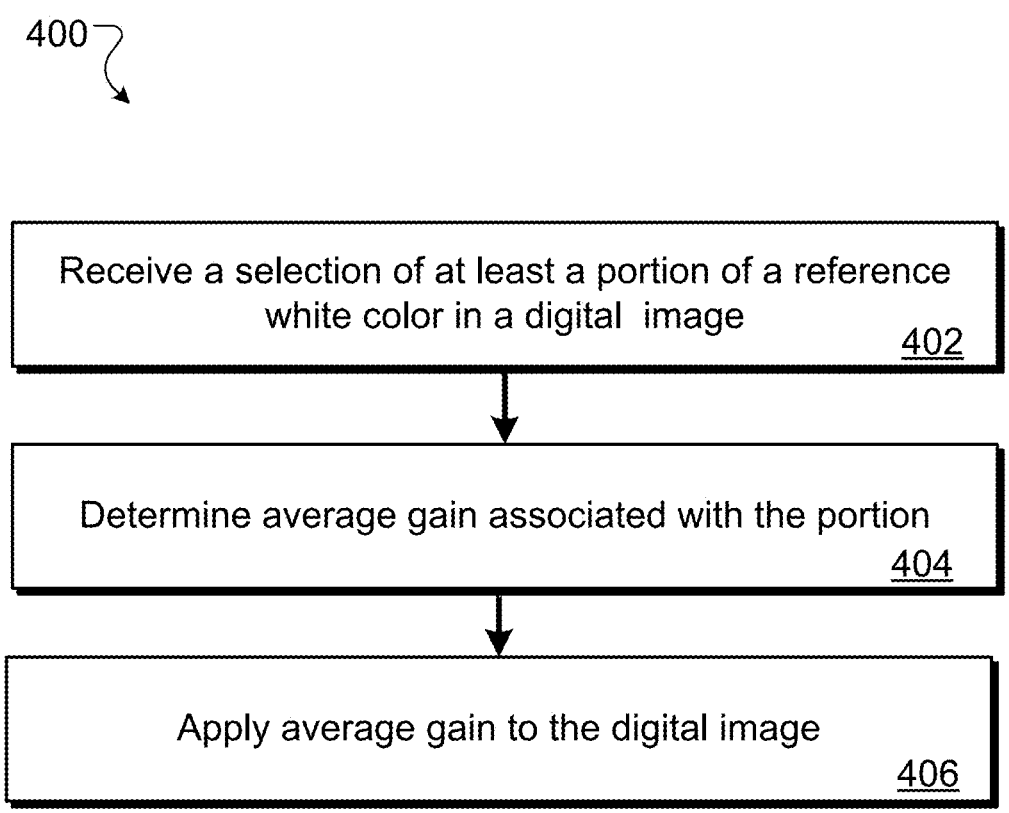
FIG. 4 is a flowchart representing example sequence of operations for normalizing gain in a digital image.

FIG. 4 is a flowchart representing an example sequence of operations for normalizing gain in a digital image. In some implementations, at least some of the operations depicted in FIG. 4 are executed in the color score calculation module 115 described with reference to FIG. 1. The operations can also be performed in a separate preprocessing module.

Operations can include receiving a selection of at least a portion of a reference white color in a digital image (402). In some implementations, a user can manually select the reference white area through a user interface such as the user interface 118 described with reference to FIG. 1. The white reference area can be selected by a digital selector tool substantially similar to the digital selector described with reference to FIG. 3A. In some implementations, the white reference can be automatically selected. For example, if a reference white marker is positioned such that the marker always appears in a predetermined position (e.g., upper left hand corner) within an image, the pixels corresponding to the predetermined position can be automatically selected as representing the reference white.

In some implementations, areas with specular reflection are avoided in selecting the white reference. For the conjunctival case, all the areas with specular reflection (the red, green and blue values are all above 220) were discarded in the redness evaluation. In some implementations, another color can be used as a reference. For example, in determining color score to determine a degree of corneal neovascularization, a non-vascularized area can be selected as the reference.

Operations can also include determining an average gain associated with pixels within the reference white area (404). Determining an average gain can include, for example, calculating the average of the color components of the Cartesian color space in which the digital image is represented. For example, if the digital image is represented using the RGB color space, calculating the average gain can include determining the average red, green and blue components for a plurality of pixels within the reference white area. The plurality of pixels can include all or a subset of pixels from the reference white area.

Determining the average gain also includes converting the average Cartesian components (e.g., average red, green and blue values) into a corresponding polar coordinate based representation. In some implementations, the polar coordinate based color space is the HSV color space.

From the polar coordinate based color space representation of the average color components, the average gain for the image is determined. For example, in the HSV color space the V value corresponding to the average of the color components represents an average gain of the image.

Operations can further include applying the average gain to a plurality of pixels from the digital image (406). In some implementations, the average gain is applied for all pixels within the digital image. Alternatively, the average gain can be applied only to pixels within the region of interest that is considered for calculating the color score. Such gain adjustment allows normalizing of images from various sources and/or that are acquired under different conditions. Even though FIG. 4 describes gain adjustment via a white balance operation, it should be recognized that other color balancing operations such as gray balance or neutral balance are also within the scope of this disclosure.

Figure 5:
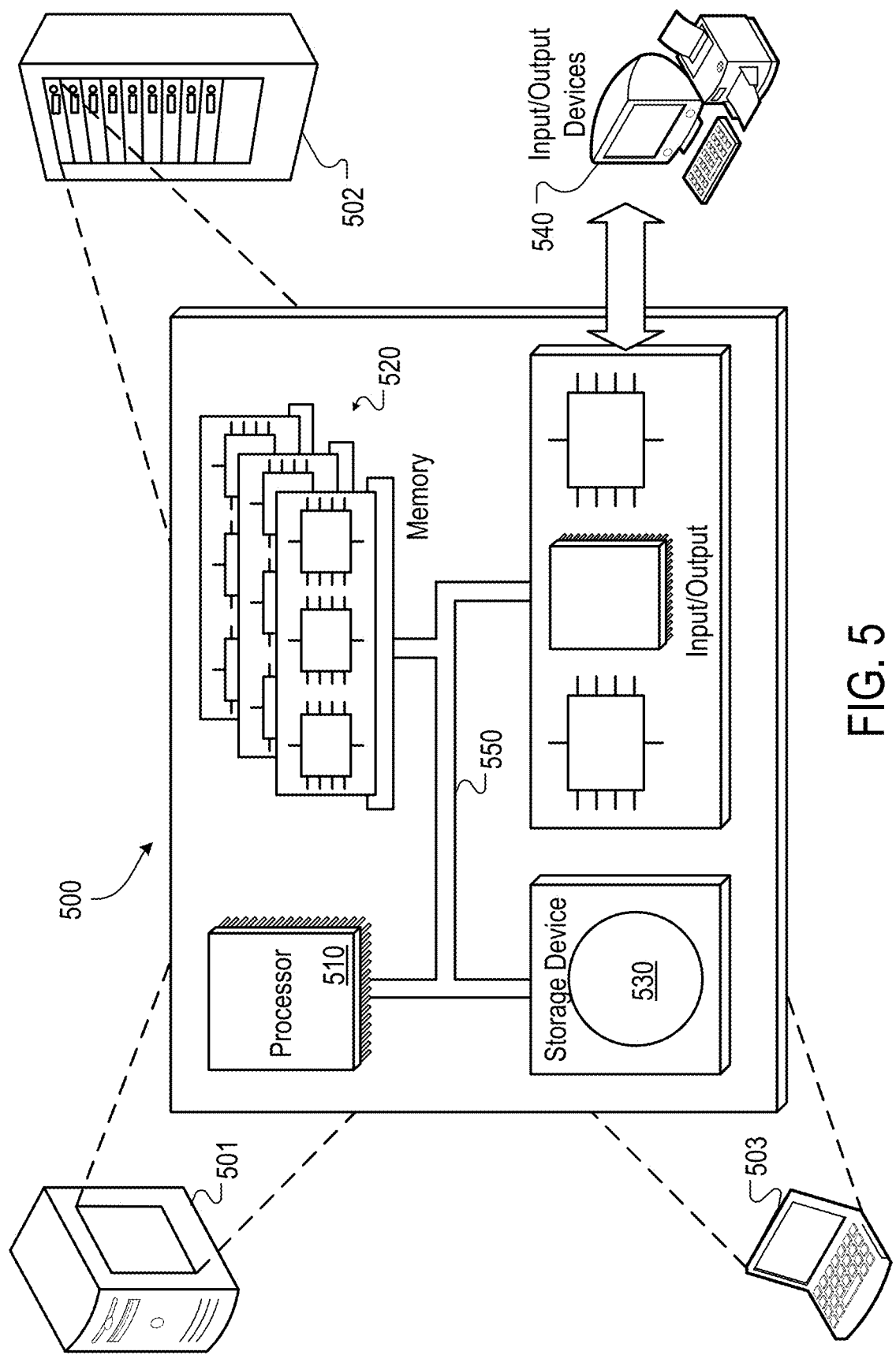
FIG. 5 is a block diagram of an example of a computing system.

FIG. 5 is a schematic diagram of a computer system 500. The system 500 can be used for the operations described with reference to the flowcharts in FIGS. 3A and 4. The system 500 can be incorporated in various computing devices such as a desktop computer 501, server 502, and/or a mobile device 503 such as a laptop computer, mobile phone, tablet computer or electronic reader device. The system 500 includes a processor 510, a memory 520, a storage device 530, and an input/output device 540. Each of the components 510, 520, 530, and 540 are interconnected using a system bus 550. The processor 510 is capable of processing instructions for execution within the system 500. In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the system 500. In some implementations, the memory 520 is a computer-readable storage medium. The memory 520 can include volatile memory and/or non-volatile memory. The storage device 530 is capable of providing mass storage for the system 500. In one implementation, the storage device 530 is a computer-readable medium. In various different implementations, the storage device 530 may be a floppy disk device, a hard disk device, an optical disk device, or a tape device.

The input/output device 540 provides input/output operations for the system 500. In some implementations, the input/output device 540 includes a keyboard and/or pointing device. In some implementations, the input/output device 540 includes a display unit for displaying graphical user interfaces. In some implementations the input/output device can be configured to accept verbal (e.g. spoken) inputs.

The features described can be implemented in digital electronic circuitry, or in computer hardware, firmware, or in combinations of these. The features can be implemented in a computer program product tangibly embodied in an information carrier, e.g., in a machine-readable storage device, for execution by a programmable processor; and features can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube), LCD (liquid crystal display) monitor, eInk display or another type of display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The processor 510 carries out instructions related to a computer program. The processor 510 may include hardware such as logic gates, adders, multipliers and counters. The processor 510 may further include a separate arithmetic logic unit (ALU) that performs arithmetic and logical operations.

The methods and systems described herein can be used in a number of clinical applications. For example, a color score can be used to determine the severity of a disorder associated with the presence of that color. Taking conjunctival redness as an example, the presence of which is associated with a number of conditions (including, but not limited to dry eye syndrome, conjunctivitis, subconjunctival hemorrhage, blepharitis, acute glaucoma, allergy, injury, keratitis, iritis, episcleritis, scleritis, uveitis, inflamed pterygium, inflamed pinguecula, airborne contaminants, tick borne illnesses like Rocky Mountain spotted fever, high stress levels and drug use including cannabis), a higher red color score (e.g., Conjunctival Redness Index (CRI)) determined by a method described herein is associated with greater severity of the condition. A lower score indicates that the condition is less severe).

The methods can also be used to monitor progression or treatment of a condition. For example, a first color score is determined at a first time point, e.g., before or during administration of a treatment for the condition associated with the presence of the color, and a second color score is determined at a later time. Again taking conjunctival redness as an example, a first red color score (e.g., CRI) is determined at a first time point, e.g., before or during treatment, and a second red color score is determined at a later time point. The two scores are then compared, and an increase in the color score indicates progression (i.e., worsening) of the condition or a lack of efficacy of the treatment; no change indicates that any treatment has at best stopped progression (in a progressive disorder), or has been ineffective; and a decrease in the color score indicates that the treatment has been effective. One of skill in the art will appreciate that the treatment will vary depending on the exact condition; common treatments include the application of cold or hot compresses; gentle washing; and administration of topical and/or systemic antibiotics, anti-inflammatories, or steroids.

EXAMPLES

Figure 6A:
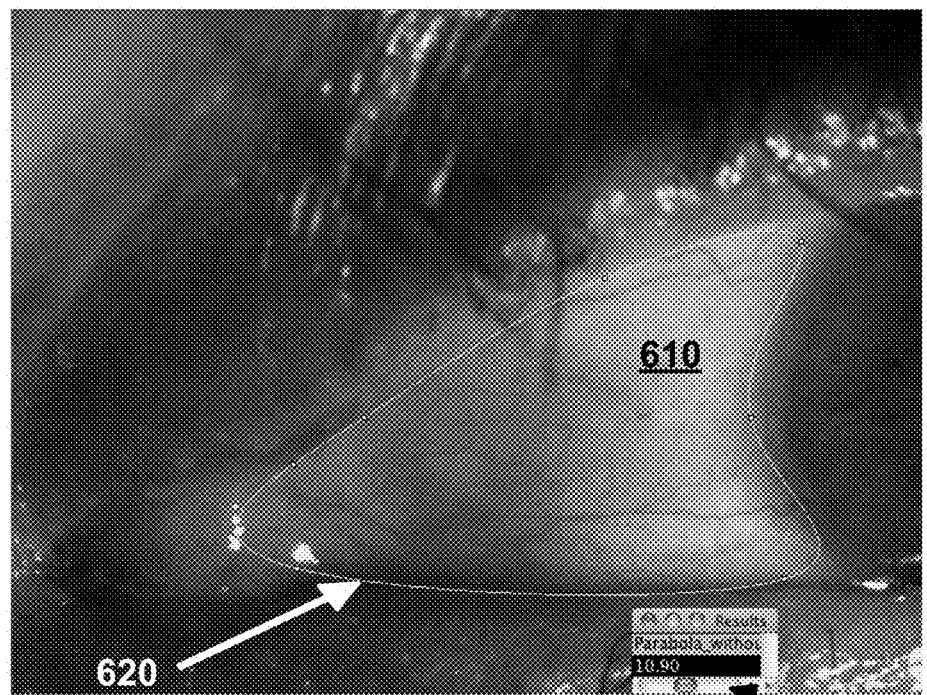
FIGS. 6A-6C are examples of images in which color scores have been calculated.
Figure 6B:
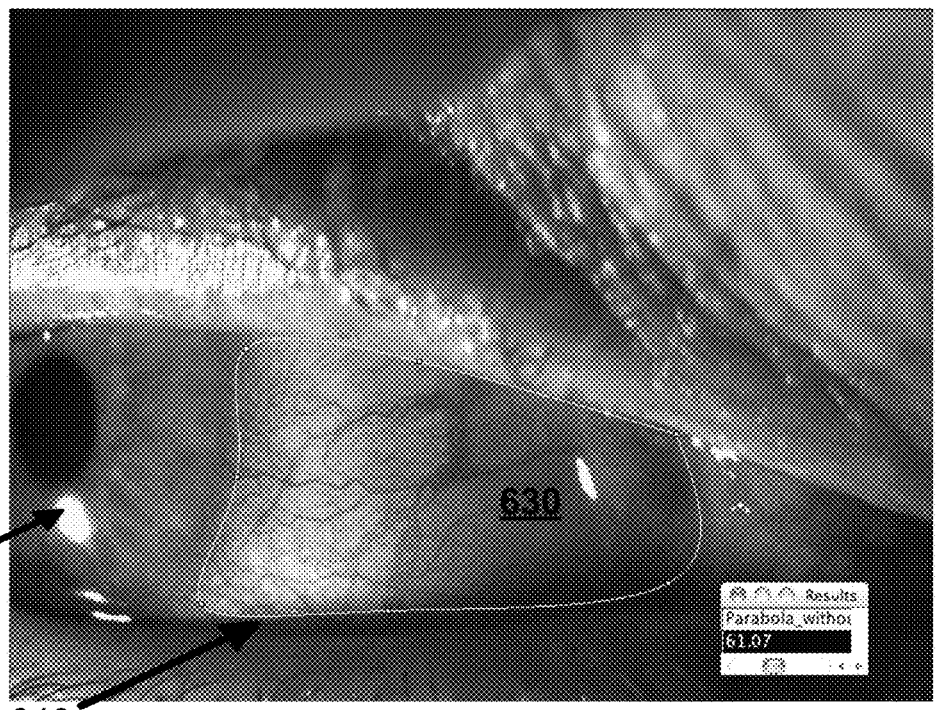
Figure 6C:
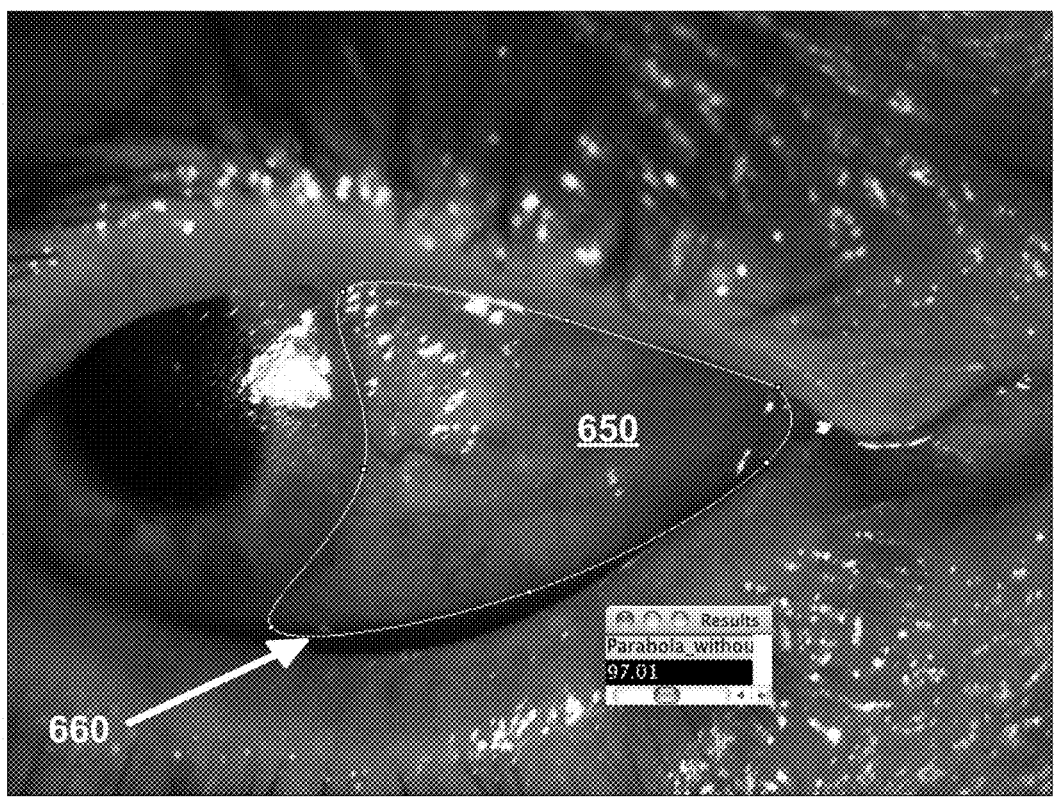

The methods and systems described herein are further described using the following examples (with reference to FIGS. 6A-6C), which do not limit the scope of the claims. FIGS. 6A-6C illustrate color score determination for conjunctival redness. The images were obtained from patients with ocular surface diseases such as dry eye disease. A Haag-Streit BQ 900 IM imaging system was used to acquire the images. The images were acquired using the same exposure and lighting parameters. However, because of the particular anatomic characteristics of each individual, angulation of the light source was customized in each case to provide good illumination and reduce confocal reflection over the area of interest.

The nasal conjunctiva of either left or right eye was captured while patients looked to the extreme ipsilateral side of the photographed eye, i.e., extreme right for right eyes or extreme left for left eyes. Images with different degrees of conjunctival redness were included in the experiment of determining the color score. Two clinicians evaluated the images and independently graded conjunctival redness based on two well-known image-based scales, the Efron (Efron, Optician. 213:26-35 (1997); Efron, Optician 219: 44-45 (2000)) and Validated Bulbar Redness (VBR; Schulze et al., Optom Vis Sci. 2007; 84:976-983; see also Schulze et al., Invest. Ophthalmol. Vis. Sci. 52(8):5812-5817 (2011)) scales. Conjunctival redness for the same images was also evaluated using the methods and systems described herein. For example, in FIG. 6A, the region 610 was selected as the evaluation area using the digital selector curve 620. For the image shown in FIG. 6B, the region 630 was selected as the evaluation area using the digital selector curve 640. Similarly, in FIG. 6C, the region 650 was selected as the evaluation area using the digital selector curve 660.

The algorithm was implemented on the Java-based imaging-processing platform ImageJ (National Institutes of Health; Rasband, ImageJ, U.S. National Institutes of Health, Bethesda, Md.; USA (imagej.nih.gov/ij/), 1997-2011; Abramoff et al., Biophotonics International (11)7:36-42 (2004)) as two plugins, one for white balancing and other for redness quantification. All images were exported from the slit-lamp camera of the imaging system as TIFF files to a personal computer executing ImageJ and the above mentioned plug-ins.

In these examples, because no reference white markers (strips) were used during image acquisition, a white spot from a white area in each of the images was selected as the reference for the white-balancing (avoiding hyper-white areas such as the spot 635 in FIG. 6B caused by confocal reflection of the light source).

The digital selector tool used for these experiments included seven adjustable points that were selected using a mouse pointer. The selector tool included left or right options depending on the side of the eye that was evaluated. The selector tool was used to select the evaluation area as the exposed nasal or temporal conjunctiva visible in the respective images. In general, for all images, the conjunctival area was selected as the area of interest excluding the cornea, lids or eyelashes from the selected evaluation area.

Figure 7A:
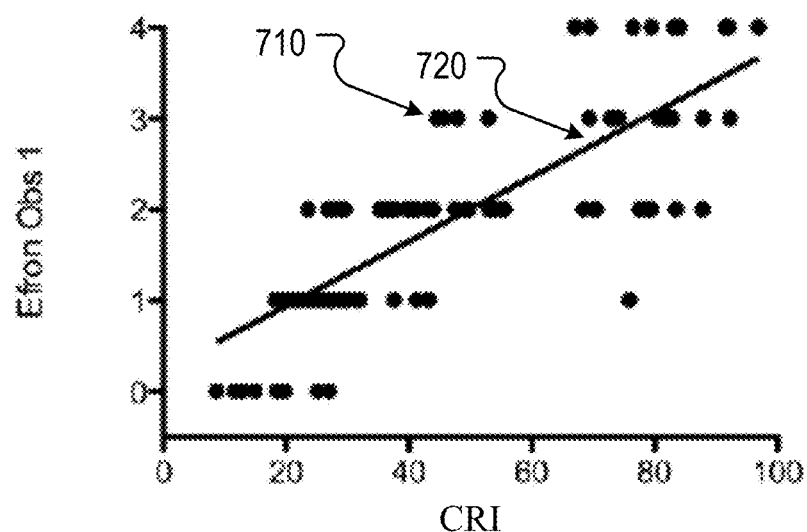
FIGS. 7A-7D show results illustrating a relationship between calculated redness scores and clinician evaluations.
Figure 7B:
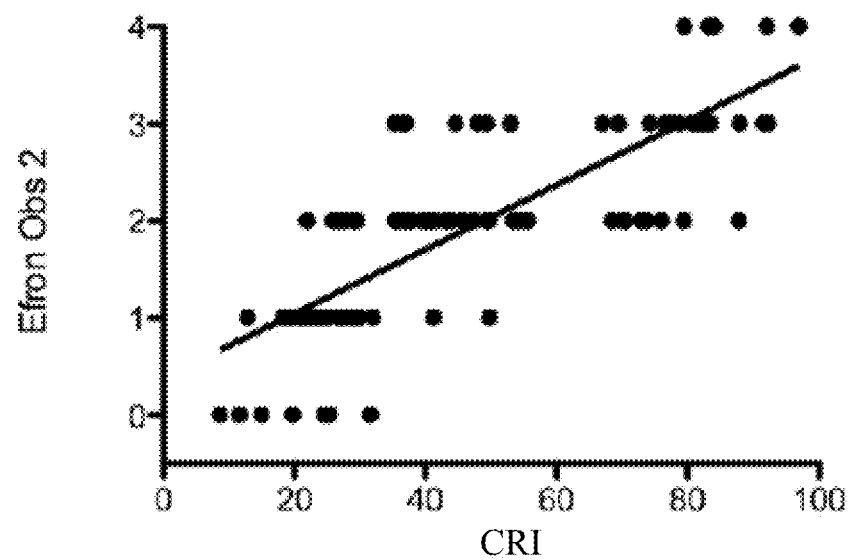
Figure 7C:
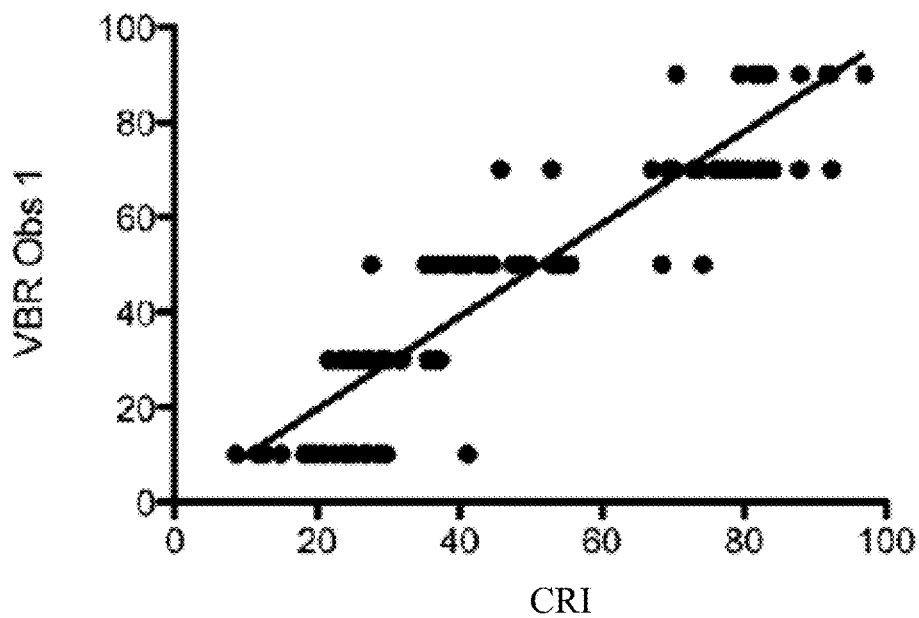
Figure 7D:
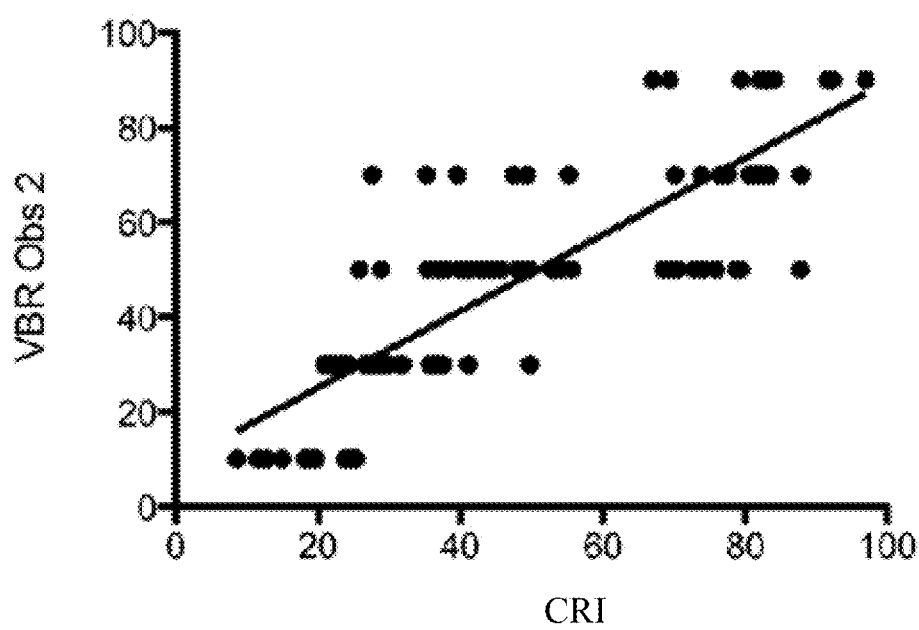

After all the images were scored, a table with all the scores was exported to a spreadsheet for analysis. The scores were also displayed on the images. For example, a score display 625 on the image shown in FIG. 6A indicated a redness score of 10.90. Similarly the image shown in FIG. 6B received a score of 61.07 and the image shown in FIG. 6C received a score of 97.01. The redness scores were then correlated with the corresponding subjective scores from the two clinical examiners for each one of the two subjective grading scales. The results for the Efron scale from the two clinical examiners are shown in FIGS. 7A and 7B, respectively. The results for the VBR scale from the two clinical examiners are shown in FIGS. 7C and 7D, respectively. FIG. 7A shows a plot in which each evaluated photograph (represented by a dot 710) is represented in a coordinate system where the y-axis represents the Efron values assigned by the clinical examiner and the x-axis represents the CRI values. The plot 720 represents a regression line fitted on the data. A metric known as the Spearman's coefficient of correlation (R) was computed based on the data. The coefficient of correlation is a metric that represents the degree of co-variation between two variables, and indicates the degree to which two variable's movements are associated. The value of R varies between $-1.0$ and $1.0$. An R value of $1.0$ indicates that there is perfect correlation between the scores of both variables. An R value of $-1.0$ indicates perfect correlation in the magnitude of the scores of both variables but in the opposite direction. On the other hand, an R value of 0 indicates that there is no correlation between the scores of the two variables. For the data set represented in FIG. 7A, the R value was 0.925, thus indicating that the CRI values were strongly correlated to the Efron value evaluations of the first clinical examiner. FIG. 7B represents the Efron value evaluation data from the second clinical examiner and in this case the R value was 0.857. FIG. 7C represents the VBR evaluation data from the first clinical examiner and in this case the R value was 0.830. FIG. 7D represents the VBR evaluation data from the second clinical examiner and in this case the R value was 0821. All of the above correlations were computed to be statistically significant ($P<0.001$). The high values of the coefficient of correlation for all the cases indicate that a strong association was found between the computer derived analysis and the subjective clinical evaluations.

Other Embodiments

A number of implementations have been described. Nevertheless, it will be understood that various modifications may be made. For example, elements of one or more implementations may be combined, deleted, modified, or supplemented to form further implementations. As yet another example, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A computer implemented method for evaluating a condition of an ocular surface based on a color of the ocular surface, the method comprising:
   obtaining a digital signal representing at least a portion of the ocular surface;
   determining, from a portion of the digital signal, a plurality of color components that are based on a Cartesian color space;
   determining, from the color components, a hue value in a polar coordinate based color space;
   selecting an angle range in the polar coordinate based color space in accordance with a color associated with the condition being evaluated;
   determining that the hue value lies within the angle range that represents the color associated with the condition being evaluated in a hue circle representation of the polar coordinate based color space;
   mapping the hue value to a scalar value within a predetermined range in response to determining that the hue value lies within the angle range;
   selecting a function of one or both of two other components of the polar coordinate based color space, wherein the function is selected based on the condition being evaluated;
   determining a color value as a product of the scalar value and the function of one or both of the two other components of the polar coordinate based color space; and
   generating a color score as a function of the color value, wherein the color score of the ocular surface relates to a quantitative evaluation of the condition of the ocular surface.

2. The method of claim 1, further comprising
   receiving a selection of at least a first portion of the digital signal;
   determining an average gain associated with the first portion of the digital signal; and
   applying the average gain to a second portion of the digital signal.

3. The method of claim 1, wherein mapping the hue value to the scalar value comprises using a parabolic curve to map the hue value to the scalar value within the predetermined range.

4. The method of claim 1, further comprising receiving a selection of a portion of the digital signal through a graphical user interface,
   wherein assigning the color score comprises assigning the color score to the portion of the digital signal.

5. The method of claim 1, wherein the color score indicates a degree of redness of the ocular surface.

6. The method of claim 1, wherein the ocular surface comprises conjunctiva.

7. The method of claim 1, wherein the Cartesian color space is an RGB color space.

8. The method of claim 1, wherein the polar coordinate based color space is an HSV color space.

9. The method of claim 1, further comprising storing the color score and an association of the color score with the digital signal.

10. The method of claim 1, wherein the digital signal is related to one or more of corneal neovascularization, fluorescein stained epithelial punctate keratitis and epithelial defects, eyelid and skin telangiectasia, and conjunctival/scleral pigmented lesions.

11. A computer readable storage device having encoded thereon computer readable instructions, which when executed by a processor, cause a processor to perform operations comprising:
   obtaining a digital signal representing at least a portion of an ocular surface;
   determining, from a portion of the digital signal, a plurality of color components that are based on a Cartesian color space;
   determining, from the color components, a hue value in a polar coordinate based color space;
   selecting an angle range in the polar coordinate based color space in accordance with a color associated with a condition of the ocular surface;
   determining that the hue value lies within the angle range that represents the color associated with the condition being evaluated in a hue circle representation of the polar coordinate based color space;
   mapping the hue value to a scalar value within a predetermined range in response to determining that the hue value lies within the angle range;
   selecting a function of one or both of two other components of the polar coordinate based color space, wherein the function is selected based on the condition being evaluated;
   determining a color value as a product of the scalar value and the function of one or both of the two other components of the polar coordinate based color space; and
   generating a color score as a function of the color value, wherein the color score of the ocular surface relates to a quantitative evaluation of the condition of the ocular surface.

12. The computer readable storage device of claim 11, further comprising
   receiving a selection of at least a first portion of the digital signal;
   determining an average gain associated with the first portion of the digital signal; and
   applying the average gain to a second portion of the digital signal.

13. The computer readable storage device of claim 11, wherein mapping the hue value to the scalar value comprises using a parabolic curve to map the hue value to the scalar value within the predetermined range.

14. The computer readable storage device of claim 11, wherein the operations further comprise receiving a selection of a portion of the digital signal through a graphical user interface,
   wherein assigning the color score comprises assigning the color score to the portion of the digital signal.

15. The computer readable storage device of claim 11, wherein the color score indicates a degree of redness of the ocular surface.

16. The computer readable storage device of claim 11, wherein the ocular surface comprises conjunctiva.

17. The computer readable storage device of claim 11, wherein the Cartesian color space is an RGB color space.

18. The computer readable storage device of claim 11, wherein the polar coordinate based color space is an HSV color space.

19. The computer readable storage device of claim 11, wherein the operations further comprise storing the color score and an association of the color score with the digital signal.

20. The computer readable storage device of claim 11, wherein the digital signal is related to one or more of corneal neovascularization, fluorescein stained epithelial punctate keratitis and epithelial defects, eyelid and skin telangiectasia, and conjunctival/scleral pigmented lesions.

* * * * *